(12) United States Patent
Wernick et al.

(10) Patent No.: US 7,469,037 B2
(45) Date of Patent: Dec. 23, 2008

(54) METHOD FOR DETECTING A MASS DENSITY IMAGE OF AN OBJECT

(75) Inventors: Miles N. Wernick, Chicago, IL (US); Yongyi Yang, Westmont, IL (US)

(73) Assignee: Illinois Institute of Technology, Chicago, IL (US)

( * ) Notice: Subject to any disclaimer, the term of this patent is extended or adjusted under 35 U.S.C. 154(b) by 0 days.

(21) Appl. No.: 11/732,343

(22) Filed: Apr. 3, 2007

(65) Prior Publication Data

US 2008/0247511 A1 Oct. 9, 2008

(51) Int. Cl.
*G01G 1/36* (2006.01)
*G21K 1/06* (2006.01)
(52) U.S. Cl. .......................................... 378/82; 378/84
(58) Field of Classification Search ............. 378/70–73, 378/80–89
See application file for complete search history.

(56) References Cited

U.S. PATENT DOCUMENTS

| 2,543,630 | A | 2/1951 | Hansen |
| 2,853,617 | A | 9/1958 | Berreman |
| 3,032,656 | A | 5/1962 | Hosemann et al. |
| 3,439,163 | A | 4/1969 | DeJongh |
| 3,628,040 | A | 12/1971 | Schnopper et al. |
| 3,777,156 | A | 12/1973 | Hammond et al. |
| 3,885,153 | A | 5/1975 | Schoenborn et al. |
| 4,223,219 | A | 9/1980 | Born et al. |
| 4,351,063 | A | 9/1982 | Dineen et al. |
| 4,599,741 | A | 7/1986 | Wittry |
| 4,625,323 | A | 11/1986 | Okaya |
| 4,649,557 | A | 3/1987 | Hornstra et al. |
| 4,737,973 | A | 4/1988 | Ogawa et al. |
| 4,949,367 | A | 8/1990 | Huizing et al. |
| 5,123,036 | A | 6/1992 | Uno et al. |
| 5,127,028 | A | 6/1992 | Wittry |
| 5,164,975 | A | 11/1992 | Steinmeyer |

(Continued)

FOREIGN PATENT DOCUMENTS

WO 95/05725 2/1995

OTHER PUBLICATIONS

D. Chapman, W. Thomlinson, R.E. Johnson, D. Washburn, E. Pisano. N. Gmür, Z. Zhong, R. Menk, F. Arfelli and D. Sayers, *X-Ray Refraction Imaging (XRI) Applied to Mammography*, published Oct. 31, 1997.

(Continued)

*Primary Examiner*—Irakli Kiknadze
(74) *Attorney, Agent, or Firm*—Pauley Petersen & Erickson

(57) ABSTRACT

A method for detecting a mass density image of an object. An x-ray beam is transmitted through the object and a transmitted beam is emitted from the object. The transmitted beam is directed at an angle of incidence upon a crystal analyzer. A diffracted beam is emitted from the crystal analyzer onto a detector and digitized. A first image of the object is detected from the diffracted beam emitted from the crystal analyzer when positioned at a first angular position. A second image of the object is detected from the diffracted beam emitted from the crystal analyzer when positioned at a second angular position. A refraction image is obtained and a regularized mathematical inversion algorithm is applied to the refraction image to obtain a mass density image.

20 Claims, 4 Drawing Sheets

U.S. PATENT DOCUMENTS

| | | | |
|---|---|---|---|
| 5,195,115 | A | 3/1993 | Schiller et al. |
| 5,245,648 | A | 9/1993 | Kinney et al. |
| 5,259,013 | A | 11/1993 | Kuriyama et al. |
| 5,319,694 | A | 6/1994 | Ingal et al. |
| 5,406,609 | A | 4/1995 | Arai et al. |
| 5,428,657 | A | 6/1995 | Papanicolopoulos et al. |
| 5,457,726 | A | 10/1995 | Miyazaki |
| 5,457,727 | A | 10/1995 | Frijlink |
| 5,579,363 | A | 11/1996 | Ingal et al. |
| 5,715,291 | A | 2/1998 | Momose |
| 5,717,733 | A | 2/1998 | Kurbatov et al. |
| 5,771,269 | A * | 6/1998 | Chao ............................ 378/5 |
| 5,787,146 | A | 7/1998 | Giebeler |
| 5,802,137 | A | 9/1998 | Wilkins |
| 5,805,662 | A | 9/1998 | Kurbatov et al. |
| 5,838,758 | A * | 11/1998 | Krug et al. .................... 378/53 |
| 5,850,425 | A | 12/1998 | Wilkins |
| 5,923,720 | A | 7/1999 | Barton et al. |
| 5,949,847 | A | 9/1999 | Terada et al. |
| 5,987,095 | A | 11/1999 | Chapman et al. |
| 6,035,227 | A | 3/2000 | Shmueli |
| 6,038,285 | A | 3/2000 | Zhong et al. |
| 6,052,433 | A * | 4/2000 | Chao ........................ 378/98.9 |
| 6,185,444 | B1 * | 2/2001 | Ackerman et al. .......... 600/410 |
| 6,192,104 | B1 * | 2/2001 | Adams et al. ................. 378/90 |
| 6,269,144 | B1 | 7/2001 | Dube et al. |
| 6,385,289 | B1 | 5/2002 | Kikuchi |
| 6,567,496 | B1 | 5/2003 | Sychev |
| 6,577,708 | B2 | 6/2003 | Chapman et al. |
| 6,804,324 | B2 | 10/2004 | Martynov et al. |
| 6,870,896 | B2 | 3/2005 | Protopopov |
| 6,947,521 | B2 | 9/2005 | Wernick et al. |
| 7,076,025 | B2 | 7/2006 | Hasnah et al. |
| 2002/0136352 | A1 | 9/2002 | Protopopov |
| 2004/0196957 | A1 | 10/2004 | Ando |

OTHER PUBLICATIONS

V.N. Ingal and E.A. Beliaevskaya, *Phase Dispersion Introscopy*, (published prior to Oct. 16, 1996).

V.N. Ingal and E.A. Beliaevskaya, X-ray plane-wave topography observation of the phase contrast from a non-crystalline object, *J. Phys. D: Appl. Phys.* 28 (1995) 2314-2317.

V.N. Ingal and E.A. Belyaevskaya, Method of phase-dispersion introscopy, *Tech. Phys.* 42 (1), Jan. 1997.

V.N. Ingal and E.A. Beliaevskaya, Phase dispersion radiography of biological objects, *Physica Medica*, vol. X11, No. 2, Apr.-Jun. 1996.

V.A. Bushuev, V.N. Ingal and E.A. Belyaevskaya, Dynamical Theory of Images Generated by Noncrystalline Objects for the Method of Phase-Dispersive Introscopy, *Crystallography Reports*, vol. 41, No. 5, 1996, pp. 766-774.

V.A. Bushuev, E.A. Beliaevskaya and V.N. Ingal, Wave-optical description of X-ray phase contrast images of weakly absorbing non-crystalline objects, *Il Nuovo Cimento*, vol. 19D, No. 2-4, Feb.-Apr. 1997.

V.N. Ingal and E.A. Beliaevskaya, Imaging of biological objects in the plane-wave diffraction scheme, *Il Nuovo Cimento*, vol. 19D, No. 2-4, Feb.-Apr. 1997.

V.N. Ingal and E.A. Beliaevskaya, Phase Dispersion Introscopy, *Surface Investigation*, vol. 12, pp. 441-450, 1997.

Tetsuya Ishikawa, Seishi Kikuta and Kazutaka Kohra, Angle-Resolved Plane Wave X-Ray Topography, *Japanese Journal of Applied Physics*, vol. 24, No. 7, Jul. 1985, pp. L559-L562.

R.C. Blasdell and A.T. Macrander, Prototype grooved and spherically bent Si backscattering crystal analyzer for meV resolution inelastic x-ray scattering, *Review of Scientific Instruments*, vol. 66, No. 2, Feb. 1995, pp. 2075-2077, New York.

Monochromatic energy-subtraction radiography using a rotating anode source and a bent Laue monochromator, a paper published in *Phys. Med. Biol.*, 42 (1997), pp. 1751-1762.

A bent Laue crystal monochromator for monochromatic radiography with an area beam, a paper published in *Nuclear Instruments and Methods in Physics Research, Section A*, 399 (1997), pp. 489-498.

Kenneth Lange et al.: EM Reconstruction Algorithms for Emission and Transmission Tomography, *Journal of Computer Assisted Tomography*, pp. 306-316, 1984.

A.P. Dempster et al.: *Maxium Likelihood from Incomplete Data via the EM Algorithm*, pp. 1-38, 1976.

Hasnah et al.: Diffraction Enhanced Imaging Contrast Mechanisms in Breast Cancer Specimens, *Medical Physics 29*, pp. 2216-2221, 2002.

\* cited by examiner

METHOD FOR DETECTING A MASS DENSITY IMAGE OF AN OBJECT

This work was supported in part by NIH/NIAMS grant AR48292 and NIH/NCI grant CA111976. Use of the National Synchrotron Light Source, Brookhaven National Laboratory, was supported by the U.S. Department of Energy, Office of Science, Office of Basic Energy Sciences, under Contract No. DE-AC02-98CH10886.

FIELD OF THE INVENTION

This invention relates to a method for detecting an image of an object, such as one mass internal with respect to another mass wherein the one mass has an absorption content, refraction content, and/or density content different from the other mass. The method of this invention measures the intensity of an x-ray beam as it emits from an object, preferably as a function of angle, and derives a mass density image from the measured intensity.

BACKGROUND OF THE INVENTION

X-ray imaging has been used in the medical field and for radiology in general, such as non-destructive testing and x-ray computed tomography. Conventional radiography systems use x-ray absorption to distinguish differences between different materials, such as normal and abnormal human tissues.

Conventional x-ray radiography measures the projected x-ray attenuation, or absorption, of an object. Attenuation differences within the object provide contrast of embedded features that can be displayed as an image. For example, cancerous tissues generally appear in conventional radiography because these tissues are more dense than the surrounding non-cancerous tissues. The best absorption contrast is generally obtained at x-ray energies where the absorption is high. Conventional radiography is typically performed using lower x-ray energy in higher doses to allow greater absorption and, thus, better contrast and images. Using x-rays having higher energy generally requires a lower dosage to be used because of patient safety concerns. In general, as the x-ray energy level increases and the x-ray dose used decreases, the quality of the conventional radiography image lessens.

Diffraction-enhanced imaging (DEI) and multiple-image radiography (MIR) are related phase-sensitive x-ray imaging methods, which generally use a system of diffracting crystals to analyze the angular components of an x-ray beam after it traverses an object. DEI can produce images depicting the effects of absorption and refraction of the beam by the object. MIR produces one additional image which shows the effect of ultra-small-angle scattering. A further advantage of MIR is that it uses a generally more-accurate imaging model.

The quantity depicted at each pixel in a DEI or MIR refraction-angle image is the angle $\Delta\theta$ by which an x-ray beam is refracted upon passing through the object. In the x-ray regime, the refractive index is always very nearly one; therefore, the measured refraction angles are very small. For example, refraction angles observed when imaging the breast are typically from about 0 to 1 µradians.

Thus, the x-component of the refraction angle can be represented by the following well-known small-angle approximation:

$$\Delta\theta(x, y) \cong \frac{\partial}{\partial x}\int_L n(x, y, z)dz, \quad (1)$$

where L is the path traversed by the beam (which is assumed to be approximately a straight line), (x,y) are spatial coordinates describing the image domain, and z is the spatial coordinate along the beam propagation direction.

Equation (1) can also be written approximately in terms of mass density as follows:

$$\Delta\theta(x, y) \cong K\frac{\partial}{\partial x}\int_L \rho(x, y, z)dz \quad (2)$$
$$\cong K\frac{\partial}{\partial x}\rho_T(x, y)$$
$$\cong 1.35 \times 10^{-6}\lambda^2 \rho_T(x, y),$$

where $K=r_e\lambda^2/4\pi u$, $r_e$ is the classical electron radius (2.82× $10^{-5}$ Å), $\lambda$ is the x-ray wavelength (in Å), u is the unified atomic mass unit (1.66×$10^{-24}$ g), and $\rho_T(x,y) \triangleq \int_L \rho(x,y,z)dz$ is the projected mass density of the object along path L (in g/cm³). Thus, since the x-ray wavelength $\lambda$ is on the order of 1 Å, it is readily seen that the refraction angle $\Delta\theta$ is on the order of 1 µradian.

The refraction-angle image produced by DEI or MIR can be very detailed and informative. An example refraction-angle image of a breast tumor (invasive carcinoma) is shown in FIG. 1. In this image, each pixel's value is equal to the angle of refraction experienced by the portion of the beam incident at a given spatial location. Thus, in FIG. 1, bright values indicate regions where the beam is refracted to the left, and dark values indicate regions where the beam is refracted to the right.

As seen in FIG. 1, refraction-angle images generally exhibit high levels of detail in the object. In part, this is due to the derivative operator inherent in the physics (see Eqs. (1) and (2)), which produces an effect equivalent to computerized edge enhancement, but without the same sensitivity to noise. However, this advantage of the refraction-angle image is also a limitation. Whereas planar medical images traditionally measure the projection of some object property (such as absorption coefficient in radiography), the refraction-angle image represents the gradient of the projected mass density, which confounds information about the mass density and its spatial distribution. In addition, because the gradient removes the DC value of the signal, it discards absolute quantitative information.

To produce an image that is more quantitatively useful than the refraction-angle image, U.S. Pat. No. 7,076,025, issued to Hasnah et al., and herein incorporated by reference in its entirety, provides a mass density image from the refraction image. For example, Equation (2) can be inverted numerically to compute the projected mass density $\rho_T(x,y)$, which has units of g/cm². The same principle can be applied to obtain the projected refractive index $n_T(x,y)=\int_L n(x,y,z)dz$.

The analytical solution of Equation (2) is simply:

$$\rho_T(x, y) = \frac{1}{K}\int_a^x \Delta\theta(x', y)dx' + C, \quad (3)$$

where the integrating constant $C=\rho_T(a,y)$ is a boundary condition representing the value of the projected density at the left edge of the image (i.e., at x=a). This boundary condition can be determined by imaging the object within a known medium, such as air, which provides a known reference at x=a.

Unfortunately, when even a modest level of noise is present, a numerical implementation of Equation (3) can yield significant artifacts (see examples in FIG. 2, center column). This limitation can be particularly relevant in clinical implementations of this technology, which may be photon-limited owing to the difficulty of producing small, bright x-ray sources. Therefore, there is a need to mitigate the effect of noise.

SUMMARY OF THE INVENTION

A general object of the invention is to provide a method for detecting an image having the contrast features of conventional radiography and using relatively high x-ray energy levels at relatively low doses, as compared to conventional radiography.

A more specific objective of the invention is to overcome one or more of the problems described above.

The general object of the invention can be attained, at least in part, through a method for providing an image of an object. The method includes obtaining a refraction image of the object, and applying a regularized mathematical inversion algorithm to the refraction image to obtain a mass density image. The regularized mathematical inversion algorithm of one embodiment is an estimation of the projected mass-density image. In one embodiment of the method of this invention, the regularized mathematical inversion algorithm comprises a constrained least-squares filter.

BRIEF DESCRIPTION OF THE DRAWINGS

These and other objects and features of this invention will be better understood from the following detailed description taken in conjunction with the drawings, wherein.

DESCRIPTION OF PREFERRED EMBODIMENTS

The method of one embodiment of this invention provides a mass density image of an object. The mass density image shows contrast features of an object, similar to conventional radiography, without relying on the absorption of x-rays by the object. The mass density image of an object is obtained through an image processing algorithm used on images based on refraction characteristics of the object, such as refraction images obtained by Diffraction Enhanced Imaging (DEI) or Multiple-Image Radiography (MIR). The refraction image for use in the method of this invention can be obtained through DEI such as, for example, the x-ray imaging method disclosed in U.S. Pat. No. 5,987,095 issued to Chapman et al. and/or in U.S. Pat. No. 6,577,708 issued to Chapman et al., or MIR such as, for example, the x-ray imaging method disclosed in U.S. Pat. No. 6,947,521 issued to Wernick et al., the entire disclosures of which are incorporated into this specification by reference.

Figure 3:
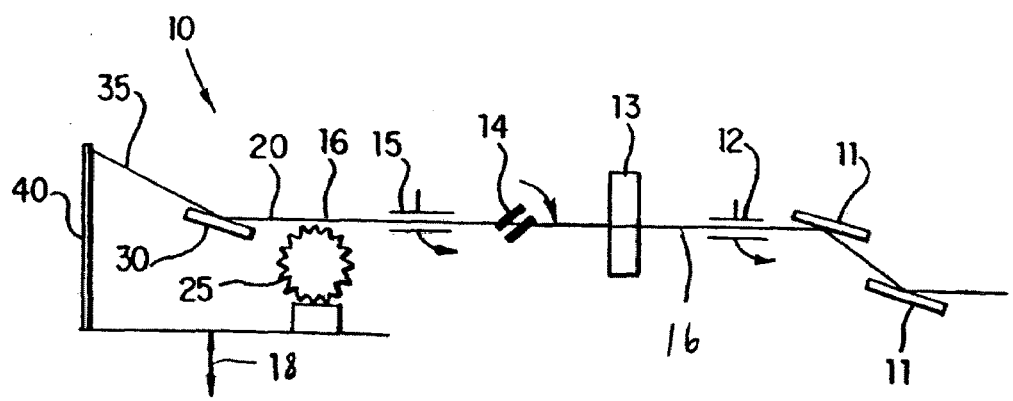
FIG. 3 is a schematic diagram of an analyzer system 10, according to one preferred embodiment of this invention.

FIG. 3 illustrates a schematic diagram of an analyzer system 10, according to one preferred embodiment of this invention. FIG. 3 is similar to the crystal analyzer system shown in FIG. 1 of U.S. Pat. No. 5,987,095, issued to Chapman et al. and FIG. 1 of U.S. Pat. No. 6,947,521, issued to Wernick et al. A crystal analyzer 30, as shown in FIG. 3, represents a Bragg type crystal analyzer. It is apparent that a Laue type analyzer or other similar type analyzer can also be used to produce the same result of generating a diffracted beam 35, for analysis purposes.

The double crystal monochromator 11 can be used to generate an x-ray beam, such as a monochromatic x-ray beam 16. In one embodiment, each crystal of the monochromator 11 is preferably constructed of silicon using a (3, 3, 3) lattice planes structure. The lattice planes used in the monochromator 11, such as the (3, 3, 3) lattice planes, desirably match those used in the crystal analyzer 30. Through experimentation, the (3, 3, 3) lattice planes structure increased the sensitivity to refraction effects by a factor of about 5, when compared to experiments conducted with (1, 1, 1) lattice planes structure. As will be appreciated by one skilled in the art following the teachings provided in this specification and in the claims, sources of monochromatic x-ray beams other than the monochromator 11 can be used to generate a monochromatic x-ray beam 16.

The mass density image is a property of the object and does not directly depend on the imaging energy. The mass density image can be derived from an imaging system, such as a DEI or MIR system, that can derive refraction angle contrast. DEI and MIR systems can typically derive refraction images using any x-ray energy level, including energy levels of approximately 40 keV or higher. According to one preferred embodiment of this invention, an x-ray beam 16 has an energy level in a range of approximately 16 keV to approximately 100 keV, more desirably approximately 18 keV to approximately 40 keV, with a bandwidth of approximately 1.5 eV. In one preferred embodiment according to this invention, the x-ray beam 16 is approximately 80 mm wide and approximately 0.1 mm high. A shutter 14, such as a rotary shutter or the like, can be used to control exposure and limit unnecessary scatter.

Any suitable detector known to those skilled in the art can be used to detect an image of an object 25. In one preferred embodiment according to this invention, the object 25 image is detected with an image plate which comprises a photo-stimulable phosphor image plate typically used for radiology, such as FUJI Medical Systems high resolution HR5 and standard resolution ST5 image plates. An image recorded on an image plate 40 can be digitized, stored and displayed, for example by a FUJI Medical Systems AC3 reader and workstation or by any other suitable digital convertor known to those skilled in the art. One suitable spatial resolution of images can be 0.1×0.1 mm².

According to one preferred embodiment of this invention, the object 25 and the image plate 40 or another suitable detector can be scanned together, such as in the directions shown by the arrow 18 in FIG. 3, to provide a two-dimensional image of the object 25 taken in the x-z plane, where the z-direction is perpendicular to the plane shown in FIG. 3. Such scanning can be accomplished, for example by a computer controlled stepper motor translation stage which holds a support for the object 25 and which also holds an image plate cassette.

Figure 1:
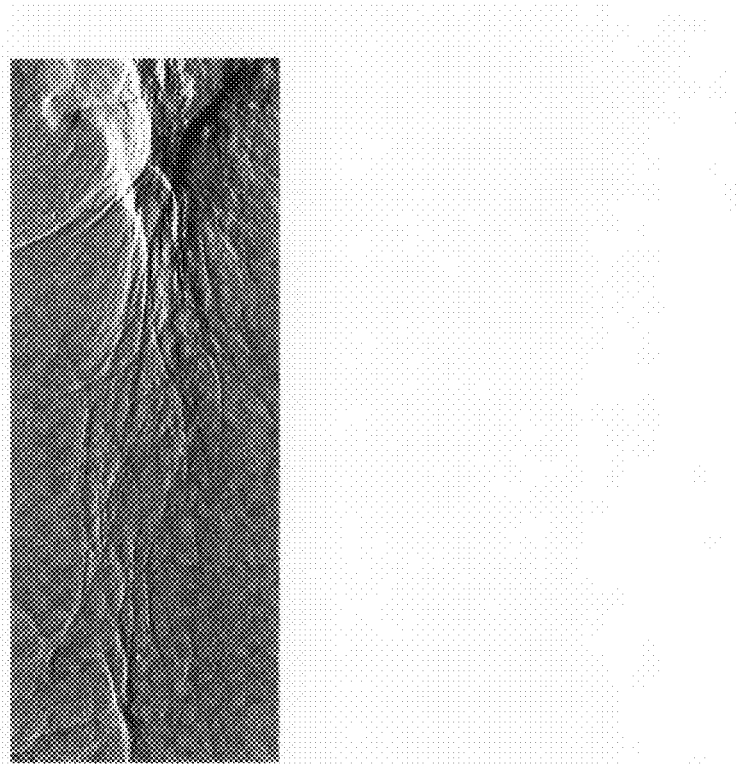
FIG. 1 is a refraction-angle image of a breast tumor (invasive carcinoma).

An ionization chamber 12 can be used downstream of the monochromator 11, for example to monitor tuning. The ionization chamber 15, as shown in FIG. 1, which is positioned upstream of the object 25, can be used to monitor a radiation dose at a surface of the object 25.

The crystal analyzer 30 is preferably positioned between the object 25 and the image plate 40. The crystal analyzer 30 is preferably fixed spatially with respect to the transmitted beam 20, oriented to diffract the transmitted beam 20 onto the image plate 40. Fine angular control of the crystal analyzer 30 can be accomplished with a stepper motor driven translation stage pushing on a relatively long rod which is mechanically connected to an axle onto which the crystal analyzer 30 is attached, or with any other suitable mechanical or electromechanical system that has fine angular control. The fine angular control may result in a resolution limit of approximately 1 microradian. Such fine tuning can position crystal analyzer 30 at various positions within the rocking curve of the crystal analyzer 30.

Figure 4:
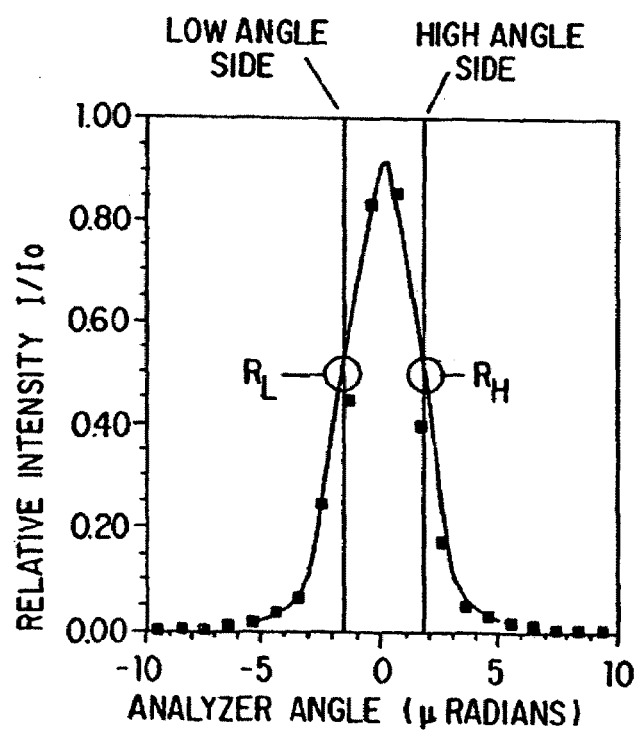
FIG. 4 shows a graphical representation of an analyzer rocking curve for a silicon Bragg type crystal analyzer having (3, 3, 3) lattice planes at an x-ray energy level of approximately 18 keV.

The crystal analyzer 30 can be used to detect the x-ray refraction angles within the transmitted beam 20 as the crystal analyzer 30 has a relatively steep intensity versus angle dependence. The intensity as a function of a crystal angle curve is called the rocking curve or the reflectivity curve. The sensitivity function of analyzer system 10, or the rocking curve of analyzer system 10, characterizes the x-ray output as a function of the angular position of analyzer system 10 when no object is present in the transmitted beam 20, as prepared by the monochromator 11. As shown in FIG. 4, the solid line curve represents a theoretical calculation of the rocking curve for crystal analyzer 30. The square points along the rocking curve represent measured points taken during an experiment conducted according to the method disclosed in U.S. Pat. No. 5,987,095.

In one embodiment according to this invention, two images (DEI) of the object 25 are detected with the image plate 40. A first image of the object 25 is detected and digitized from the diffracted beam 35 emitted from the crystal analyzer 30 at a first angular position. A second image of the object 25 is detected and digitized from the diffracted beam 35 emitted from the crystal analyzer 30 at a second angular position. In one embodiment according to this invention, the first and second angular positions are on opposing sides of the rocking curve of the crystal analyzer 30. For example, the first angular position of the crystal analyzer 30 can be at a low angle setting of the rocking curve of the crystal analyzer 30 and the second angular position of the crystal analyzer 30 can be at a high angle setting of the rocking curve of the crystal analyzer 30. The first and second images are mathematically combined to derive a mass density image of the object 25.

In one embodiment according to this invention, the first and second images are digitized and combined to derive a refraction image, and the mass density image is derived from the refraction image. The refraction image, like an absorption image obtained by conventional radiography, depends on contrast, or the density change, between two materials of object 25, such as a body embedded within a matrix material. However, the refraction image is a measure of the gradient of the projected density of the object 25. The refraction angle image depends on the spatial gradient of the thickness of the embedded object whereas a conventional absorption image depends only on the thickness.

In another embodiment of this invention, the analyzer 30 is positioned at a more than two angular positions (e.g., also at a third angular position) relative to diffracted beam 35, such as is described in U.S. Pat. No. 6,947,521, thereby allowing for the measurement of the intensity at various points of diffracted beam 35. The intensity measurements are used to determine the angular intensity spectrum within the diffracted beam 35. The angular intensity spectrum of diffracted beam 35 is determined by measuring the intensity of the transmitted beam 20 at the more than two angular positions, determining a measured angular intensity spectrum, and taking into account the sensitivity of the analyzer system 10, i.e., subtracting out the intrinsic rocking curve of the analyzer system 10.

The method of one embodiment of this invention for providing an image of an object applies a regularized mathematical inversion algorithm to a refraction image, such as obtained by the methods discussed above, to obtain a mass density image. The regularized mathematical inversion algorithm desirably includes an estimation of the projected mass-density image. The regularized mathematical inversion algorithm of this invention desirably provides improved mass-density images, particularly as compared to mass density images obtained by direct inversion (See FIG. 2), such as is disclosed in, for example, U.S. Pat. No. 7,076,025.

In one particularly preferred embodiment of this invention, the regularized mathematical inversion algorithm comprises a constrained least-squares filter for recovering a mass-density image from a refraction-angle image. The discussions below use discrete versions of the images of interest. Thus, the refraction-angle image $\Delta\theta(x,y)$ and projected density image $\rho_T(x,y)$ are replaced by discrete representations $\Delta\theta(m,n)$ and $\rho_T(m,n)$, respectively, in which (m,n) are pixel indices. The index m=0, . . . , M−1 is the discrete coordinate corresponding to the x-axis, and the index n=0, . . . , N−1 is the discrete coordinate corresponding to the y-axis. Vectors represent these discrete images by using lexicographic ordering, in which case $\Delta\theta(m,n)$ and $\rho_T(m,n)$ are denoted by vectors $\Delta\theta$ and $\rho_T$, respectively.

Thus, Equation (1) is approximated as follows:

$$\Delta\theta = D\rho_T, \tag{4}$$

where D is a matrix representing a difference operator acting along the horizontal axis of the image. Specifically, by introducing appropriate zero-padding of the image, D is defined as a doubly block-circulant matrix which has the effect of performing circular convolution with the kernel:

$$d = (1\ -1). \tag{5}$$

As will be appreciated by those skilled in the art following the teachings herein provided, the particulars of representing convolution by a doubly block-circulant matrix can be found in standard image processing texts.

The noise in $\Delta\theta$ is Gaussian-distributed. A constrained least-squares (CLS) approach is employed to invert Equation (4), which is equivalent to maximum a posteriori (MAP)

estimation of the density image under an assumption of Gaussian noise and a Gaussian prior on the true image. The following CLS objective function is formed:

$$J(\rho_T)=\|\Delta\theta-D\rho_T\|^2+\gamma\|Q\rho_T\|^2, \quad (6)$$

where $\gamma$ is a regularization parameter and Q is a doubly block-circulant matrix which represents two-dimensional convolution with the Laplacian kernel:

$$q = \begin{pmatrix} -1 \\ 2 \\ -1 \end{pmatrix}. \quad (7)$$

The purpose of the second term in Equation (6) is to regularize the inversion problem. The kernel q is a high-pass filter along the vertical axis of the image; therefore, the regularization term in Equation (6) penalizes image variations that are orthogonal to the refraction-gradient direction, thus suppressing the development of streak artifacts.

The CLS estimate of the mass-density image is given by:

$$\hat{\rho}_T = \underset{\rho_T}{\operatorname{argmin}} J(\rho_T), \quad (8)$$

which has the following well-known solution:

$$\hat{\rho}_T=(D^T D+\gamma Q^T Q)^{-1} D^T \Delta\theta. \quad (9)$$

As used herein, carets are used to denote estimated quantities.

While the matrix representations used in the preceding equations are helpful for analytical purposes, it is easier to perform these expressions as convolutions in the Fourier domain. Since D and Q are doubly block-circulant, they are diagonalized by the two-dimensional discrete Fourier transform (DFT), which is defined as:

$$F(k, l) = \sum_{m=0}^{M-1}\sum_{n=0}^{N-1} f(m, n)\exp\left[-j2\pi\left(\frac{mk}{M}+\frac{nl}{N}\right)\right], \quad (10)$$

$$k = 0, \ldots, M-1$$
$$l = 0, \ldots, N-1$$

for an M×N image f(m,n). Thus, Equation (9) can be transformed to the DFT domain to obtain a form similar to that of the classical Wiener filter:

$$\hat{P}_T(k, l) = \frac{D^*(k, l)}{|D(k, l)|^2 + \gamma|Q(k, l)|^2}\Delta\Theta(k, l), \quad (11)$$

where $\hat{P}_{T,0}(k,l)$, $D(k,l)$, $Q(k,l)$, $\Delta\Theta(k,l)$ are the 2D DFTs of $\hat{\rho}_{T,0}(m,n)$, $d(m,n)$, $q(m,n)$, and $\Delta\theta(m,n)$, respectively.

For operators D and Q, $D(k,l)=0$ when $k=0$, and $Q(k,l)=0$ when $l=0$. Consequently, it is not possible to recover the DC component of $\hat{P}_T(k,l)$. This is not surprising because the difference operator D has removed the DC component from each row of the original image. In order to obtain a meaningful recovery of the DC component of the original signal, additional prior information is exploited, such as the known boundary values used in the direction inversion method in Equation (3).

Thus, the general solution for the mass density image is obtained as:

$$\hat{\rho}_T(m,n)=\hat{\rho}_{T,0}(m,n)+\hat{\rho}_T^*(n), \quad (12)$$

where $\hat{\rho}_T^*(n)$ is an estimate of the DC value of row n, and $\hat{\rho}_{T,0}(m,n)$ is obtained from the inverse DFT of $\hat{P}_T(k,l)$ in Equation (11) with $\hat{P}_T(0,0)$ set to zero. That is, $$\hat{\rho}_{T,0}(m,n)=DFT^{-1}\{\hat{P}_T(k,l)\}, \quad (13)$$

where $\hat{P}_T(0,0)=0$.

To complete the solution, the DC value $\hat{\rho}_T^*(n)$ is estimated. If the object is surrounded on one side by air or water, then pixels in this region provide a known reference value. In this case, it is known a priori that the projected mass density in this region should be $\rho_{T,ref}(x,y)=\int_L\rho_{ref}(x,y,z)dz=\rho_{ref}t$, where $\rho_{ref}$ is the density of the reference medium, and t is the thickness of the reference medium traversed by the beam.

The DC value $\hat{\rho}_T^*(n)$ can be calculated from $\hat{\rho}_{T,0}(1, n)$, $n=1, \ldots, N$. However, in the presence of noise, relying on a single pixel to form the estimate of the DC value is generally not desirable. Instead, all the image values in a B×N rectangular reference region lying along the left edge of the image are used to estimate the $\hat{\rho}_T^*(n)$ as follows:

$$\hat{\rho}_T^*(n) = \rho_{ref}t - \frac{1}{B}\sum_{m=1}^{B}\hat{\rho}_{T,0}(m, n). \quad (14)$$

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

To demonstrate the method and resulting image of this invention a numerical phantom was created, consisting of a small sphere of known mass density immersed in a homogeneous medium. To understand the factors determining the accuracy of mass-density estimation, the following experimental variables of the phantom and imaging procedure were varied: the radius R of the sphere, the difference $\Delta\rho$ between the mass density of the sphere and that of the surrounding medium, the intensity of the incident x-ray beam (determining the noise level), and the regularization parameter $\gamma$.

The method of this invention improves DEI and MIR methods for use with, for example, diagnostic imaging of the breast or other soft tissue, where density variations are small and absorption contrast is very low. With this in mind, the sphere radius R ranged from 0.5 mm to 5 mm, the mass-density difference $\Delta\rho$ ranged from 0.04 g/cm$^3$ to 0.2 g/cm$^3$, and the absorption coefficient of the sphere equal was set to that of the surrounding material. The mass density differences studied were similar to that typically encountered in actual breast tissue. The absorption coefficient only determines the local noise level in the image, so its local variations play a secondary role and thus were not considered.

Implementations of DEI and MIR are generally photon-limited, so two beam intensity levels were considered, yielding 250 ph/pixel and 1000 ph/pixel, respectively, when the object is absent. The parameter $\gamma$ was varied from 0 to 20, to determine the optimal value. To simulate the effect of photon noise, simulated noise was introduced into the refraction-angle image. The noise in a given pixel of a DEI refraction-angle image is generally Gaussian, with zero mean, and variance given by:

$$\text{var}(\Delta\theta) = \frac{1}{2I_R}\left(\frac{R(\theta_L)}{\left[\frac{dR}{d\theta}(\theta_L)\right]^2} - \frac{(\overline{\Delta\theta})^2}{R(\theta_L)}\right), \quad (15)$$

in which $\overline{\Delta\theta}$ is the true value of the refraction angle at the given pixel, $R(\theta)$ is the intrinsic rocking curve of the crystal optics system, and $\theta_L$ is the angular position at which one of the raw DEI images is acquired, and $I_r(x,y) \cong I_0 \exp(-\int_L \mu(x,y,z)dz)$ is the attenuated beam intensity (in units of photons), in which $\mu(x,y,z)$ is the absorption coefficient distribution of the object and $I_0$ is the incident beam intensity. In Equation (15) it is assumed that the two raw images that are used to perform DEI are acquired at symmetric points on the rocking curve. Acquisition of the raw images at symmetric points on the rocking curve is generally necessary to obtain unbiased estimates of the refraction angle.

Simulated-Data Image Results

Figure 2:
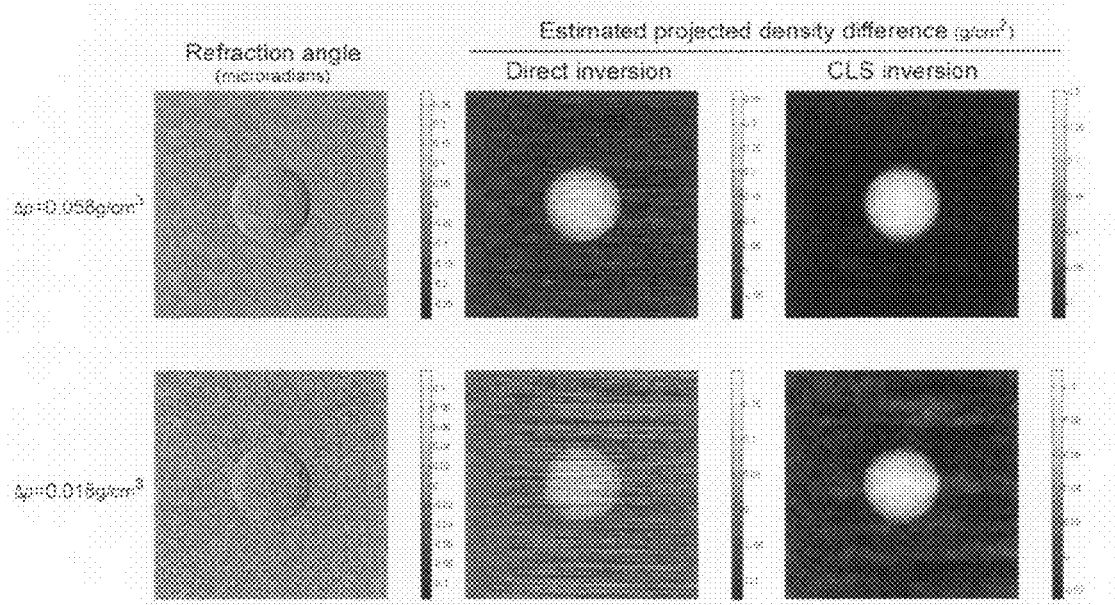
FIG. 2 includes refraction-angle images and reconstructed mass-density images of simulated sphere phantom of radius 2.5 mm with $I_0=1000$ ph/pixel. The images in the top row represent the mass-density difference between a breast tumor and average breast tissue; the images in the bottom row represent the difference between a mass and adipose tissue. In the higher-contrast case (top row), the CLS inversion according to the method of this invention virtually eliminates the streak artifacts, but some colored noise remains in the lower-contrast case (bottom row).

FIG. 2 shows examples of simulated refraction-angle images of the sphere phantom, along with mass density images reconstructed using the CLS algorithm according to this invention and the direction inversion formula in Equation (3). Results are shown for two different values of the mass-density difference $\Delta\rho$ between the sphere and the surrounding medium. The value $\Delta\rho=0.058$ g/cm³ is typical of the difference between a tumor mass and average breast tissue. The value $\Delta\rho=0.018$ g/cm³ is typical of the difference between a mass and adipose tissue. The results shown are for a combination of beam intensity and integration time that yields $I_0=1000$ ph/pixel when the object is not present, which, at the assumed x-ray energy of 30 keV, corresponds to a surface dose for water of 0.03 mGy. In the simulations, the pixel size is 50 μm and the region of interest studied is 15 mm×15 mm.

The CLS algorithm performs well in eliminating the streak artifacts that arise from using Equation (3). In addition, the CLS algorithm yields estimated mass-density variations that are quantitatively accurate, as are demonstrated below.

Accuracy of Mass Density Estimation

To measure the quantitative accuracy of mass density estimation, it was assumed that the radius of the sphere is known, and the mass-density difference at each pixel within the sphere was estimated as follows:

$$\hat{\Delta\rho}(m,n) = \frac{\hat{\rho}_T(m,n) - \rho_{medium}}{2\sqrt{R^2 - r^2}}, (m,n) \in S \quad (16)$$

where $\rho_{medium}$ is the mass density of the medium in which the sphere is immersed, r is the distance from pixel (m,n) to the center of the sphere, and S is the set of pixels in which the sphere appears. The mass-density of the sphere material was then estimated as:

$$\hat{\Delta\rho} = \frac{1}{N_S}\sum_{(m,n)\in S}\hat{\Delta\rho}(m,n), \quad (17)$$

where $N_S$ is the number of pixels in S.

To quantify estimation accuracy, the percent root-mean-square (% RMS) error was used, which we defined as follows:

$$\% \text{ RMS} = 100 \times \frac{\sqrt{E[(\hat{\Delta\rho} - \Delta\rho)^2]}}{\Delta\rho}, \quad (18)$$

where E[•] denotes an ensemble average over 20 noise realizations.

Figure 5:
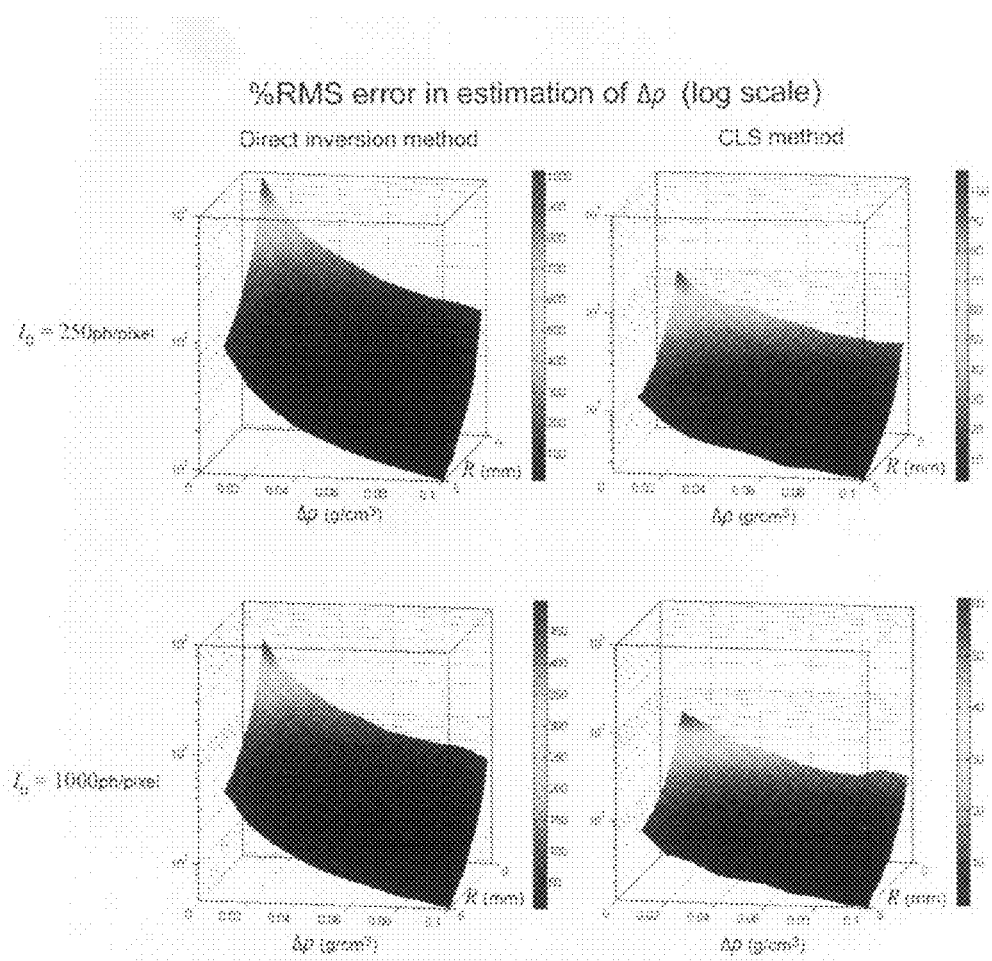
FIG. 5 is plots of percent root-mean-square (% RMS) error of the estimated mass density as a function of the sphere radius R and mass density difference $\Delta\rho$.

FIG. 5 is plots of the % RMS error achieved by the best choice of γ for the two different noise levels in the data. The % RMS error is plotted on a logarithmic scale so that the entire dynamic range can be clearly seen. The accuracy of estimation improves as the sphere radius or the density difference becomes larger. For small spheres with weak density variation $\Delta\rho$, the CLS method improved the estimation accuracy by as much as an order of magnitude. For large, high-contrast objects (R=5 mm, $\Delta\rho$=0.2 g/cm³), the CLS algorithm provided % RMS error as low as about 2%.

The best choice of γ ranged from 0.5 to 5. The optimal value was obtained by trial and error. However, as will be appreciated by those skilled in the art following the teachings herein provided, there are well-known iterative approaches to automating the selection of the regularization parameter in CLS algorithms that can be used.

Real-data Image Results

Figure 6:
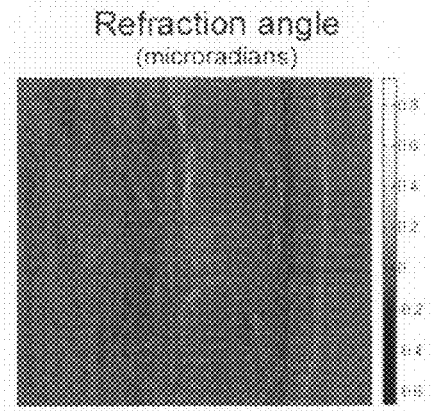
FIG. 6 is a refraction-angle image a breast specimen acquired using a synchrotron x-ray source.

FIG. 6 is an example of an MIR refraction-angle image of a breast specimen, containing an invasive breast cancer, which was mounted in a 4-cm-thick water tank. The image was computed from data acquired using 40 keV x-rays at the National Synchrotron Light Source at Brookhaven National Laboratory. A higher exposure was used than in the simulated data described above, which was measured as 3.5 mGy. The MIR data were acquired over a range of ±4 microradians.

Figure 7:
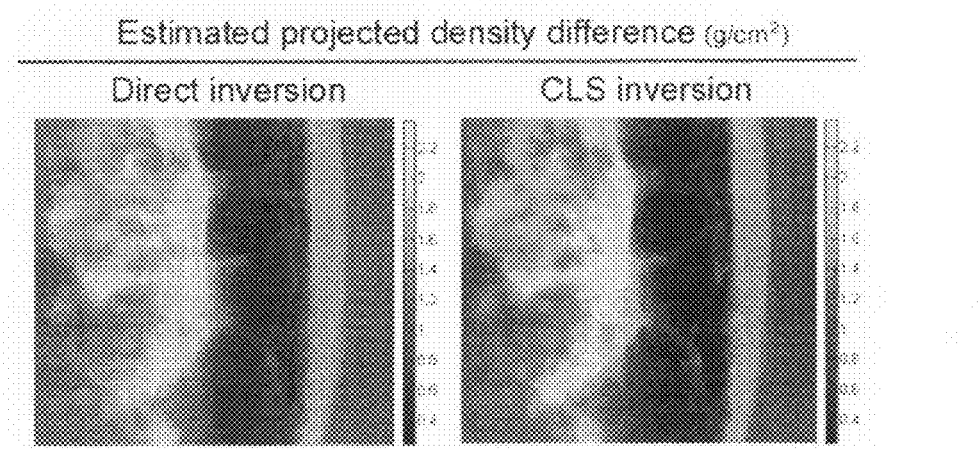
FIG. 7 is mass-density images of a breast specimen computed from the nearly noise-free refraction-angle image in FIG. 6.

Because a synchrotron was used with an ample exposure, the refraction-angle image is virtually noise-free. Even so, when this image is used to compute a mass-density image by the direct inversion method in Equation (3), noticeable streak artifacts are obtained (FIG. 7, left), which are effectively eliminated by the method of this invention (FIG. 7, "CLS Inversion"). In this example, the specimen was surrounded on the left side by water, which served as the reference medium used by both algorithms.

Thus the method of this invention provides accurate images of mass density from a MIR or DEI refraction-angle image, such as by using constrained least-squares (CLS) estimation. The CLS approach of this invention mitigates the potential problem of streak artifacts that are obtained by attempting to invert the model of the refraction-angle image directly by integration. The method of this invention has been shown to be successful in suppressing streak artifacts, and to improve quantitative accuracy significantly. The mass-density images provided by the method of this invention will find application in, for example, breast imaging, for quantification of lesion, in estimation of bone loss in aging patients, or in the detection of water uptake resulting from osteoarthritis.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A method for providing an image of an object, comprising:
   obtaining a refraction image of the object;
   applying a regularized mathematical inversion algorithm to the refraction image to obtain a mass density image; and
   displaying the obtained mass density image.

2. The method of claim 1, wherein the regularized mathematical inversion algorithm comprises a constrained least-squares filter.

3. The method of claim 1, wherein the regularized mathematical inversion algorithm comprises an estimation of the projected mass-density image.

4. The method of claim 1, wherein the regularized mathematical inversion algorithm comprises estimation of the projected mass-density image $\hat{\rho}_T(m,n)$ by using:

$$\hat{\rho}_T(m, n) = \hat{\rho}_{T,0}(m, n) + \hat{\rho}_T^*(n),$$

wherein $$\hat{\rho}_{T,0}(m, n) = DFT^{-1}\{\hat{P}_T(k, l)\}$$

wherein $$\hat{P}_T(k, l) = \frac{D^*(k, l)}{|D(k, l)|^2 + \gamma|Q(k, l)|^2}\Delta\Theta(k, l),$$

where $DFT^{-1}$ denotes the two-dimensional inverse discrete Fourier transform in terms of discrete frequencies (k,l) with $\hat{P}_T(0,0)$ set to zero, and $$\hat{\rho}_T^*(n) = \rho_{ref}t - \frac{1}{B}\sum_{m=1}^{B}\hat{\rho}_{T,0}(m, n),$$

wherein $\rho_{ref}t$ is the known projected mass density of the material appearing in a reference region that is B pixels wide and lies outside the object.

5. A method for providing an image of an object, comprising:
   obtaining a refraction image of the object, wherein obtaining the refraction image comprises:
      transmitting an x-ray beam through the object and emitting from the object a transmitted beam;
      directing the transmitted beam at an angle of incidence upon a crystal analyzer;
      detecting a first image of the object from a first diffracted beam emitted from the crystal analyzer positioned at a first angular position;
      detecting a second image of the object from a second diffracted beam emitted from the crystal analyzer positioned at a second angular position; and
      combining the first image and the second image to derive the refraction image;
   applying a regularized mathematical inversion algorithm to the refraction image to obtain a mass density image; and
   displaying the obtained mass density image.

6. The method of claim 5, further comprising:
   detecting a third image of the object from a third diffracted beam emitted from the crystal analyzer positioned at a third angular position; and
   combining the first image, the second image, and the third image to derive a refraction image.

7. The method of claim 5, further comprising:
   detecting the first image of the object from the first diffracted beam emitted from the crystal analyzer at a low rocking curve angle setting of the crystal analyzer; and
   detecting the second image of the object from the second diffracted beam emitted from the crystal analyzer at a high rocking curve angle setting of the crystal analyzer.

8. The method of claim 5, wherein the first image and the second image are exposed on a detector capable of producing a digitized image.

9. The method of claim 8, wherein the exposed first image and the exposed second image are digitized.

10. The method of claim 9, wherein the digitized images are mathematically combined to form a digitized refraction image.

11. The method of claim 10, wherein the refraction image and the mass density image are defined on a pixel-by-pixel basis.

12. The method of claim 5, wherein the x-ray beam has an energy level of at least about 16 keV.

13. The method of claim 5, wherein the x-ray beam has an energy level of at least about 40 keV.

14. The method of claim 5 wherein the x-ray beam has an energy level in a range of approximately 16 keV to approximately 100 keV.

15. The method of claim 5 wherein the x-ray beam is diffracted by a monochromator which is matched in orientation and lattice planes to the crystal analyzer.

16. The method of claim 5 further comprising increasing a relative intensity of the image of the object by adjusting an angular position of the crystal analyzer.

17. The method of claim 16 wherein the angular position of the crystal analyzer is adjusted in steps of approximately 1 microradian increments.

18. The method of claim 5, wherein the x-ray beam is monochromatic.

19. The method of claim 5, wherein the regularized mathematical inversion algorithm comprises a constrained least-squares filter.

20. The method of claim 5, wherein the regularized mathematical inversion algorithm comprises an estimation of the projected mass-density image.

* * * * *